US012084643B2

(12) United States Patent
Lee et al.

(10) Patent No.: US 12,084,643 B2
(45) Date of Patent: Sep. 10, 2024

(54) APPARATUS FOR MEASURING ELECTROPHYSIOLOGICAL SIGNAL OF THREE-DIMENSIONAL CELL AND METHOD OF FABRICATING THE SAME

(71) Applicant: KOREA ADVANCED INSTITUTE OF SCIENCE AND TECHNOLOGY, Daejeon (KR)

(72) Inventors: Hyunjoo Lee, Daejeon (KR); Chaeyun Shim, Daejeon (KR); Yehhyun Jo, Daejeon (KR); Kiup Kim, Daejeon (KR); Joo-Hyeon Lee, Daejeon (KR); Eunyoung Jang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 789 days.

(21) Appl. No.: 17/082,344

(22) Filed: Oct. 28, 2020

(65) Prior Publication Data

US 2021/0403845 A1 Dec. 30, 2021

(30) Foreign Application Priority Data

Jun. 29, 2020 (KR) .................. 10-2020-0079268

(51) Int. Cl.
*C12M 1/00* (2006.01)
*B01L 3/00* (2006.01)
(Continued)

(52) U.S. Cl.
CPC .............. *C12M 23/26* (2013.01); *B01L 3/505* (2013.01); *C12M 23/12* (2013.01); *C12M 41/00* (2013.01);
(Continued)

(58) Field of Classification Search
CPC ......... B01L 2200/12; B01L 2300/0609; B01L 2300/0848; B01L 2300/123; B01L 3/505;
(Continued)

(56) References Cited

U.S. PATENT DOCUMENTS 5,563,067 A 10/1996 Sugihara et al.
2015/0079670 A1* 3/2015 Domansky .......... B05B 17/0646
435/283.1

FOREIGN PATENT DOCUMENTS

JP 2019219244 A 12/2019
KR 101490966 B1 2/2015
KR 20150079147 A 7/2015

OTHER PUBLICATIONS

Shim et al., "Highly Stretchable Microelectrode Array for Free-Form 3D Neuronal Tissue," Mems 2020, The 33rd IEEE International Conference on Micro Electro Mechanical Systems, Jan. 18-22, 2020, 7 pages.
(Continued)

*Primary Examiner* — Lydia Edwards
(74) *Attorney, Agent, or Firm* — Hoffman Warnick LLC

(57) ABSTRACT

An apparatus for measuring an electrophysiological signal of a three-dimensional (3D) cell and a method of fabricating the apparatus. The apparatus includes a flexible substrate including a plurality of protrusions, and a conductor formed on the plurality of protrusions, and regions other than the plurality of protrusions are partially removed from the flexible substrate.

5 Claims, 20 Drawing Sheets

(51) Int. Cl.
- *B01L 99/00* (2010.01)
- *C12M 1/32* (2006.01)
- *C12M 1/34* (2006.01)
- *G01N 15/1031* (2024.01)
- *G01N 15/12* (2024.01)

(52) U.S. Cl.
CPC ... *B01L 2200/12* (2013.01); *B01L 2300/0609* (2013.01); *B01L 2300/0848* (2013.01); *B01L 2300/123* (2013.01)

(58) Field of Classification Search
CPC ...... C12M 23/12; C12M 23/26; C12M 41/00; C12M 41/46
See application file for complete search history.

(56) References Cited

OTHER PUBLICATIONS

Boehler et al., "Nanostructured platinum grass enables superior impedance reduction for neural microelectrodes," Elsevier, Biomaterials, 67, 2015, 346-353.
Hu et al., "Stretchable ultrasonic transducer arrays for three-dimensional imaging on complex surfaces," Science Advances, Research Article, 2018, 12 pages.

* cited by examiner

APPARATUS FOR MEASURING ELECTROPHYSIOLOGICAL SIGNAL OF THREE-DIMENSIONAL CELL AND METHOD OF FABRICATING THE SAME

CROSS-REFERENCE TO RELATED APPLICATION(S)

This application claims the benefit of Korean Patent Application No. 10-2020-0079268, filed on Jun. 29, 2020, in the Korean Intellectual Property Office, the disclosure of which is incorporated herein by reference.

BACKGROUND

1. Field of the Invention

One or more example embodiments relate to an apparatus for measuring an electrophysiological signal of a three-dimensional (3D) cell and a method of fabricating the same.

2. Description of the Related Art

Since an existing system for measuring an electrophysiological signal of a three-dimensional (3D) cell is invasively inserted into a 3D cell to measure an electrophysiological signal or supplying of media is not smoothly performed due to a structure of a planar electrode, it is disadvantageous in measurement of signals for a relatively long period of time and it is also difficult to measure signals in various regions of the 3D cell.

In an electrophysiological signal measurement system according to a related art, since microelectrodes fail to be in close contact with 3D cells, or to have flexibility or stretchability, it may be impossible to accurately measure an electrophysiological signal.

SUMMARY

The following example embodiments provide technology of measuring an electrophysiological signal of a three-dimensional (3D) cell.

According to an example embodiment, an electrophysiological signal measurement apparatus includes a flexible substrate including a plurality of protrusions, and a conductor formed on the plurality of protrusions, wherein regions other than the plurality of protrusions are partially removed from the flexible substrate.

The flexible substrate may be formed of a polymer.

The polymer may include a polyimide.

The conductor may include at least one of gold (Au), silver (Ag), platinum (Pt), titanium (Ti), iridium (Ir), and iridium oxide (IrOx).

The flexible substrate may have a serpentine structure in which the plurality of protrusions are connected to each other via serpentine lines.

The flexible substrate may have a cantilever structure in which the plurality of protrusions are centered.

The electrophysiological signal measurement apparatus may further include a cell culture well, and the flexible substrate may be connected to an inner side of the cell culture well.

According to another example embodiment, an electrophysiological signal measurement apparatus includes an electrode pocket formed by combining a first flexible substrate and a second flexible substrate, wherein each of the first flexible substrate and the second flexible substrate includes a plurality of protrusions, a conductor is formed on the plurality of protrusions, and regions other than the plurality of protrusions are partially removed from each of the first flexible substrate and the second flexible substrate.

The flexible substrate may be formed of a polymer.

The polymer may include polyimide.

The conductor may include at least one of Au, Ag, Pt, Ti, Ir, and IrOx.

The first flexible substrate and the second flexible substrate may each have a serpentine structure in which the plurality of protrusions are connected to each other via serpentine lines.

The first flexible substrate and the second flexible substrate may each have a cantilever structure in which the plurality of protrusions are centered.

The electrophysiological signal measurement apparatus may further include a cell culture well, and the electrode pocket may be connected to an inner side of the cell culture well.

According to another example embodiment, a method of fabricating an electrophysiological signal measurement apparatus includes forming a flexible substrate, generating a plurality of protrusions by etching the flexible substrate, partially removing regions other than the plurality of protrusions from the flexible substrate, and forming a conductor on the plurality of protrusions.

The generating of the plurality of protrusions may include forming a photoresist layer on the flexible substrate, allowing the photoresist layer to overflow by heating the photoresist layer, and generating the plurality of protrusions by etching the flexible substrate based on the overflowing photoresist layer.

The allowing of the photoresist layer to overflow may include adjusting a slope of the photoresist layer based on a heating time and a heating temperature.

The partially removing of the regions other than the plurality of protrusions may include forming a metal mask layer on the flexible substrate in which the plurality of protrusions are formed, partially etching the regions other than the plurality of protrusions in the flexible substrate based on the metal mask layer, and removing the metal mask layer.

The method may further include providing a sacrificial layer under the flexible substrate.

The method may further include removing the sacrificial layer, after the forming of the conductor.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1A:
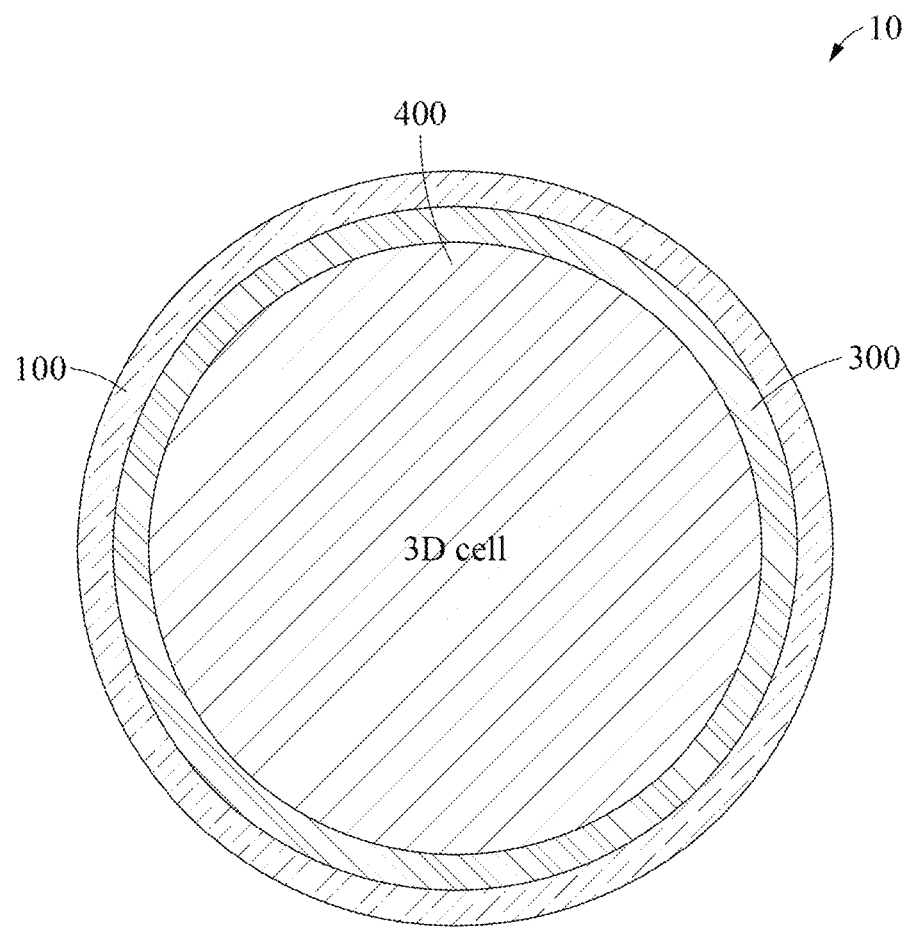
FIG. 1A illustrates an example of an electrophysiological signal measurement apparatus according to an example embodiment.

Hereinafter, some example embodiments will be described in detail with reference to the accompanying drawings. Various modifications may be made to the example embodiments. Here, the example embodiments are not construed as limited to the disclosure and should be understood to include all changes, equivalents, and replacements within the idea and the technical scope of the disclosure.

The terminology used herein is for the purpose of describing example embodiments only and is not intended to be limiting. As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

Also, the terms "first," "second," "A," "B," "(a)," "(b)," and the like may be used herein to describe components according to example embodiments. Each of these terminologies is not used to define an essence, order or sequence of a corresponding component but used merely to distinguish the corresponding component from other component (s). It should be noted that if it is described in the specification that one component is "connected", "coupled", or "joined" to another component, a third component may be "connected", "coupled", and "joined" between the first and second components, although the first component may be directly connected, coupled or joined to the second component.

A component having a common function with a component included in one example embodiment is described using a like name in another example embodiment. Unless otherwise described, description made in one example embodiment may be applicable to another example embodiment and detailed description within a duplicate range is omitted. FIG. 1A illustrates an example of an apparatus (hereinafter, referred to as an "electrophysiological signal measurement apparatus") for measuring an electrophysiological signal according to an example embodiment, and FIG. 1B illustrates a side of the electrophysiological signal measurement apparatus of FIG. 1A.

Figure 1B:
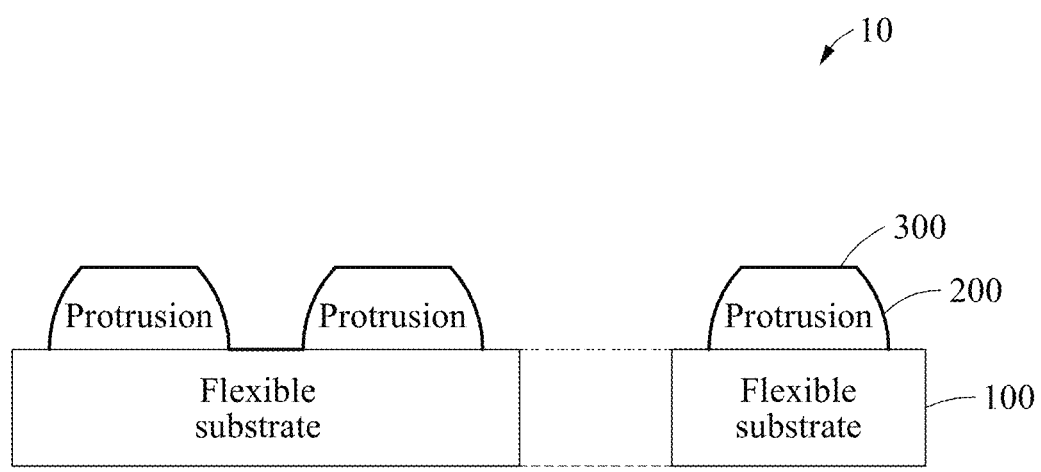
FIG. 1B illustrates a side of the electrophysiological signal measurement apparatus of FIG. 1A.

Referring to FIGS. 1A and 1B, an electrophysiological signal measurement apparatus 10 may measure an electrophysiological signal of a biological tissue. An electrophysiological signal may refer to an electric signal associated with physiology of living organisms. The electrophysiological signal may include an electric signal associated with a physiological movement of biological tissues of living organisms. For example, the electrophysiological signal may include an electrocardiogram signal, an electroencephalogram signal, and an electrooculogram signal. Biological tissues of living organisms may include cells of living organisms.

The electrophysiological signal measurement apparatus 10 may non-invasively measure an electrophysiological signal. The electrophysiological signal measurement apparatus 10 may smoothly measure an electrophysiological signal of a cell having a three-dimensional (3D) structure using a flexible substrate.

The electrophysiological signal measurement apparatus 10 may measure an electrophysiological signal generated in a 3D cell by enclosing the 3D cell using an electrode pocket structure (or a microelectrode pocket structure) having flexibility and stretchability.

The electrophysiological signal measurement apparatus 10 may non-invasively measure electrophysiological signals of 3D cells having various shapes. Also, the electrophysiological signal measurement apparatus 10 may measure electrophysiological signals for a relatively long period of time by having a pattern that facilitates supplying media for culturing cells.

For example, the electrophysiological signal measurement apparatus 10 may be used in research for treatment of various diseases using 3D cells such as a brain organoid or a spheroid of cardiomyocytes.

The electrophysiological signal measurement apparatus 10 may form an electrode pocket structure through a microelectromechanical systems (MEMS) process, to smoothly measure an electrophysiological signal while increasing an area of a contact with a 3D cell, in comparison to a microelectrode with a planar structure.

The electrophysiological signal measurement apparatus 10 may measure electrophysiological signals of cells while culturing the cells for a relatively long period of time by smoothly supplying media to the cells through a space between electrodes. Also, the electrophysiological signal measurement apparatus 10 may be compatible with an existing cell culture system.

The electrophysiological signal measurement apparatus 10 may include a flexible substrate 100, and a conductor 300 formed on the flexible substrate 100. The electrophysiological signal measurement apparatus 10 may measure an electrophysiological signal of a 3D cell 400 using the conductor 300.

The flexible substrate 100 may include a plurality of protrusions 200, and the conductor 300 may be formed on the plurality of protrusions 200 and/or a portion that does not protrude from the flexible substrate 100. Regions other than the protrusions 200 may be partially removed from the flexible substrate 100.

By removing a portion of the flexible substrate 100, the electrophysiological signal measurement apparatus 10 may increase flexibility or stretchability of the flexible substrate 100, and may allow the protrusions 200 and the conductor 300 formed on a plane to be in close contact with a 3D curved surface of the 3D cell 400.

The electrophysiological signal measurement apparatus 10 may further include a cell culture well. The flexible substrate 100 may be connected to an inner side of the cell culture well. In other words, the electrophysiological signal measurement apparatus 10 may measure physiological signals of cells while culturing the cells. The cell culture well will be further described below with reference to FIGS. 9 through 11B.

The flexible substrate 100 may be formed of a polymer. The polymer may include, for example, a polyimide. As the polymer, other materials with flexibility may also be used. For example, a flexible substrate may be formed of a transparent polyimide.

The conductor 300 may include a metal conductor and a non-metal conductor. For example, the conductor 300 may include at least one of gold (Au), silver (Ag), platinum (Pt), titanium (Ti), iridium (Ir), and iridium oxide (IrOx). The conductor 300 may also be formed on the flexible substrate 100, not the protrusions 200.

The flexible substrate 100 may have a pattern to secure flexibility and stretchability. In an example, the flexible substrate 100 may have a serpentine structure in which the plurality of protrusions 200 are connected to each other via serpentine lines. In another example, the flexible substrate 100 may have a cantilever structure in which the plurality of protrusions 200 are centered.

The flexible substrate 100 may be formed using a combination of the serpentine structure and the cantilever structure. A pattern of the flexible substrate 100 will be further described below with reference to FIGS. 3A through 4B.

Hereinafter, a structure of the electrophysiological signal measurement apparatus 10 of FIG. 1A will be described with reference to FIGS. 2 through 6.

Figure 2:
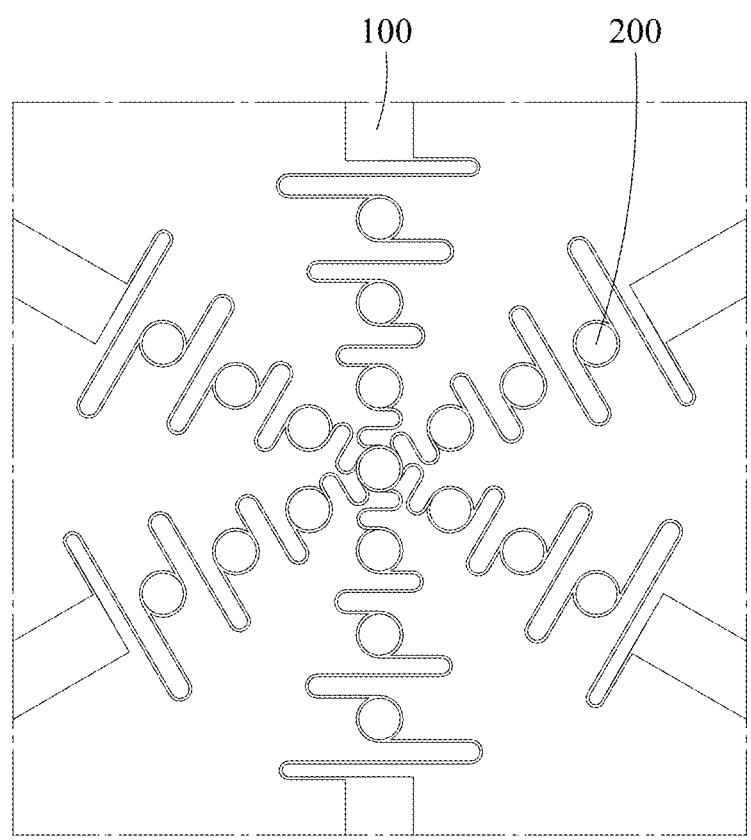
FIG. 2 is a plan view of the electrophysiological signal measurement apparatus of FIG. 1A.
Figure 3A:
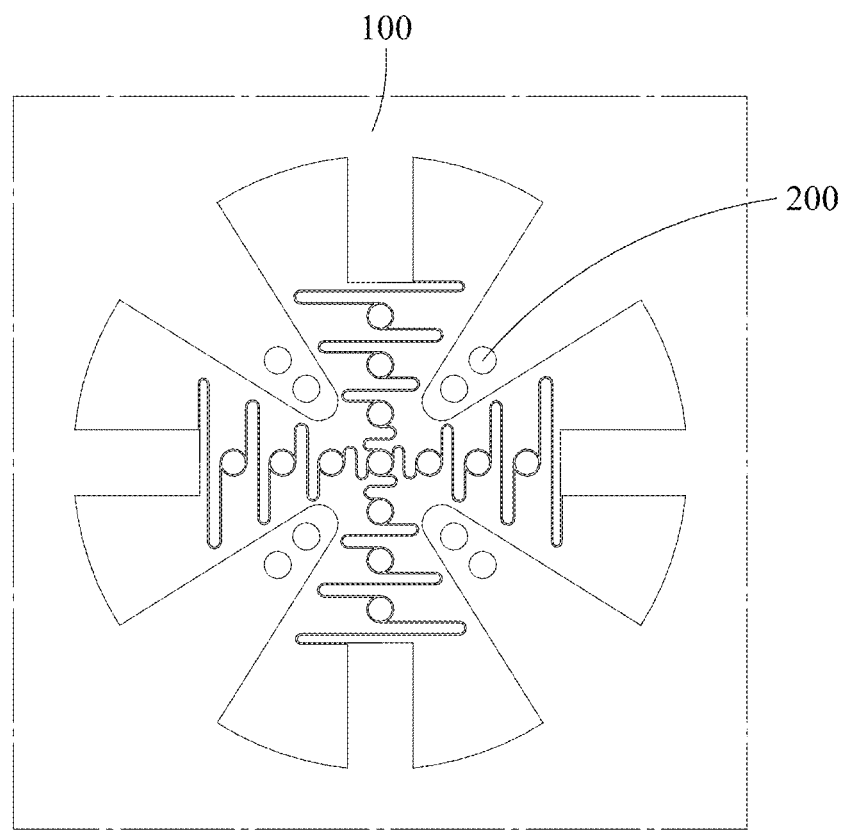
FIG. 3A illustrates an example of a flexible and stretchable pattern of the electrophysiological signal measurement apparatus of FIG. 1A.
Figure 3B:
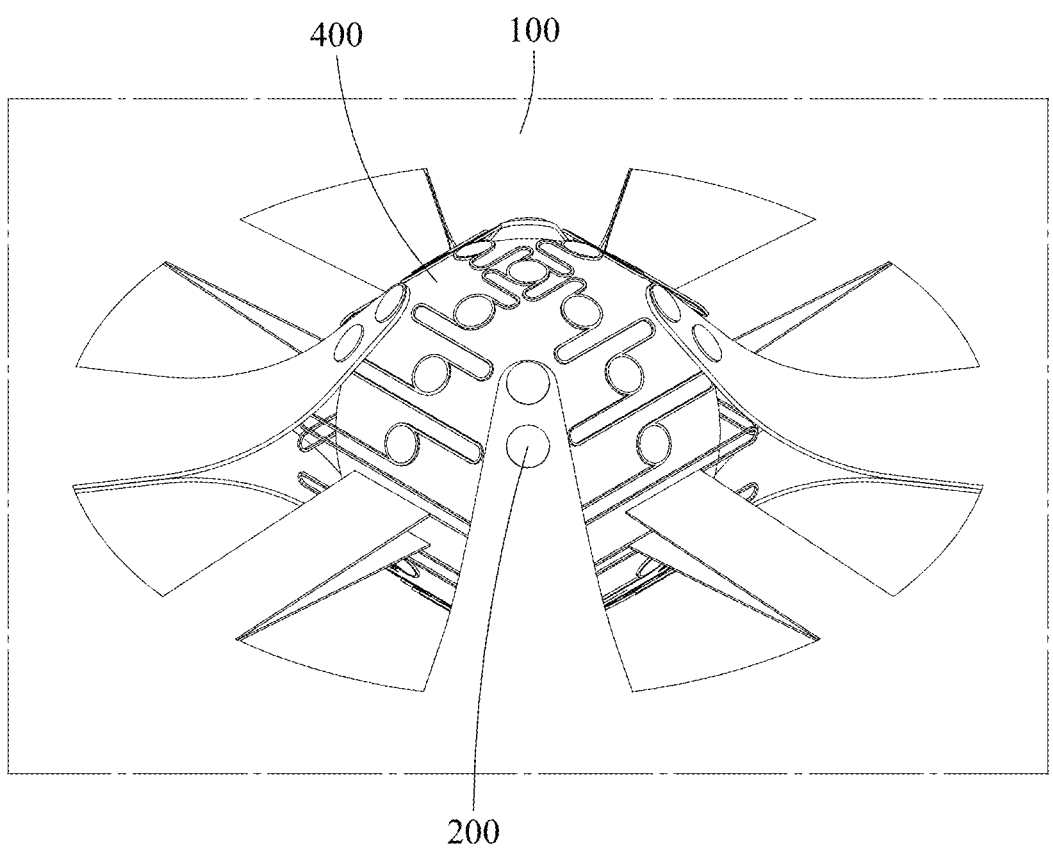
FIG. 3B illustrates an example of an electrode pocket formed using the flexible and stretchable pattern of FIG. 3A.
Figure 4A:
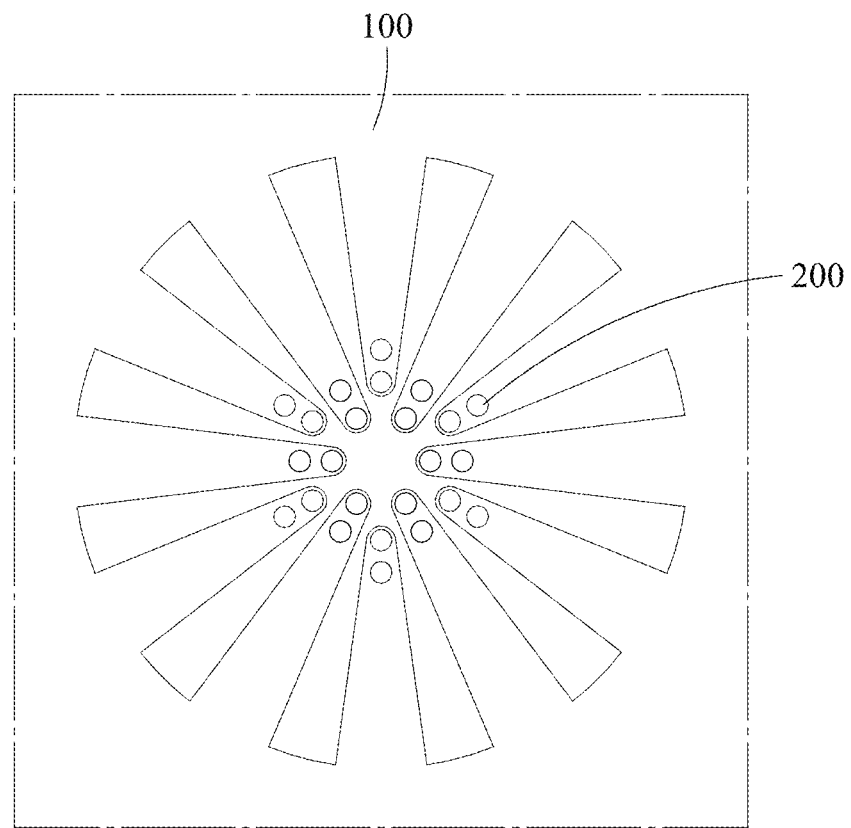
FIG. 4A illustrates another example of a flexible and stretchable pattern of the electrophysiological signal measurement apparatus of FIG. 1A.
Figure 4B:
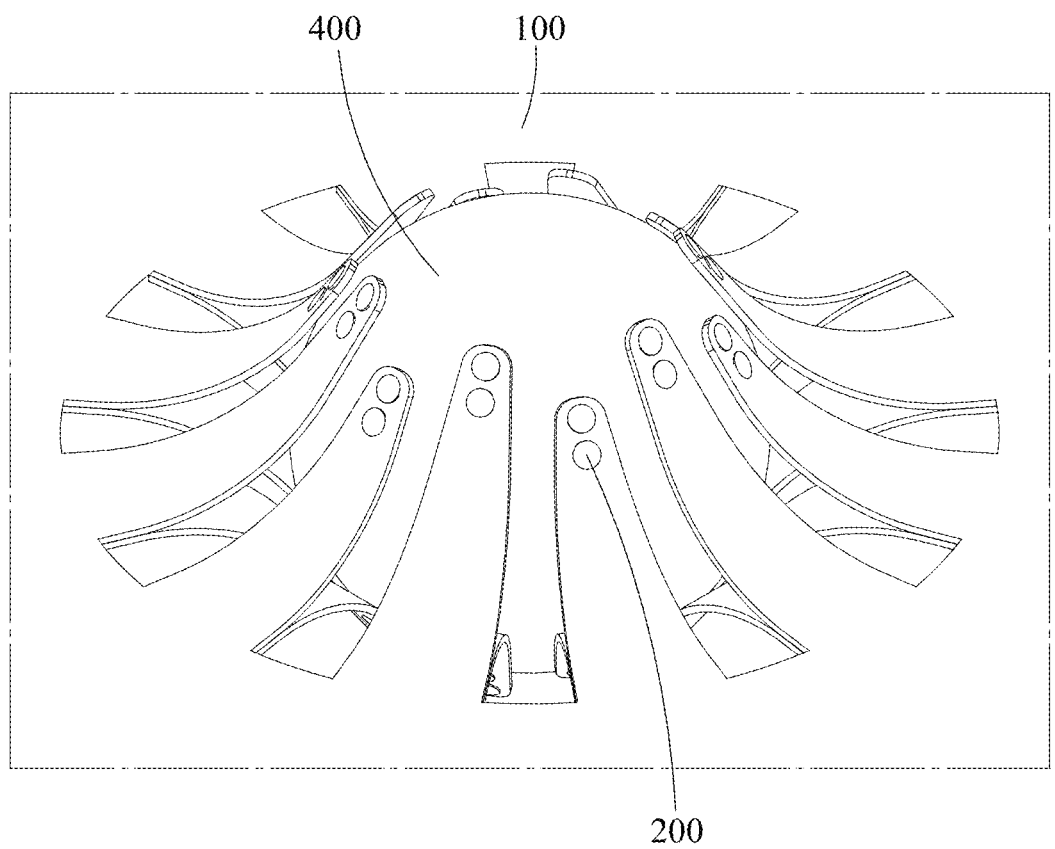
FIG. 4B illustrates an example of an electrode pocket formed using the flexible and stretchable pattern of FIG. 4A.

FIG. 2 is a plan view of the electrophysiological signal measurement apparatus 10 of FIG. 1A. FIGS. 3A and 4A illustrate examples of flexible and stretchable patterns of the electrophysiological signal measurement apparatus 10, and FIGS. 3B and 4B illustrate examples of electrode pockets formed using the flexible and stretchable patterns of FIGS. 3A and 4A, respectively.

Referring to FIGS. 2 through 4B, the electrophysiological signal measurement apparatus 10 may non-invasively measure an electrophysiological signal of the 3D cell 400 using a microelectrode pocket structure with the flexible and stretchable pattern.

The electrophysiological signal measurement apparatus 10 may include the flexible substrate 100, and the plurality of protrusions 200 formed on the flexible substrate 100. The conductor 300 may be formed on the protrusions 200.

The conductor 300 may also be formed on portions other than the protrusions 200 in the flexible substrate 100. For example, the conductor 300 may also be formed on a curved portion of the flexible substrate 100 in FIG. 2.

A portion of regions other than the protrusions 200 may be removed from the flexible substrate 100. The flexible substrate 100 may be formed to have various flexible and/or stretchable patterns, for example, a serpentine structure or a cantilever structure.

FIG. 2 illustrates a state in which regions, excluding the flexible substrate 100, the protrusions 200 and a portion of the flexible substrate 100 connecting the protrusions 200, are removed. In FIG. 2, the electrophysiological signal measurement apparatus 10 has a serpentine structure in which the protrusions 200 are connected to each other via serpentine lines. In FIG. 2, the protrusions 200 are connected via curves, and thus the electrophysiological signal measurement apparatus 10 may have flexibility and stretchability.

FIG. 3A illustrates an example of the flexible and stretchable pattern of the electrophysiological signal measurement apparatus 10 of FIG. 1A. The electrophysiological signal measurement apparatus 10 of FIG. 3A has a structure in which a serpentine structure and a cantilever structure are combined. In FIG. 3A, a flexible substrate 100 (for example, a transparent polyimide) may be in a form of a patterned serpentine structure and may have great stretchability. FIG. 3A illustrates an example of the electrophysiological signal measurement apparatus 10 in which the protrusions 200 of the flexible substrate 100 are connected in a serpentine structure and to which a cantilever structure in which a pattern facing outwards from a central portion is removed is applied.

FIG. 3B illustrates an example of an electrode pocket formed using the flexible and stretchable pattern of FIG. 3A. When a structure of a microelectrode pocket enclosing a 3D cell 400 is formed as shown in FIG. 3B, a shape of the 3D cell 400 in the microelectrode pocket may not be significantly modified. Since the serpentine structure has openings, media may be smoothly supplied to the 3D cell 400.

FIG. 4A illustrates another example of the flexible and stretchable pattern of the electrophysiological signal measurement apparatus 10 of FIG. 1A. In FIG. 4A, the electrophysiological signal measurement apparatus 10 has a pattern using a cantilever structure. In FIG. 4A, the plurality of protrusions 200 may be formed on the flexible substrate 100, and a portion of regions other than the protrusions 200 may be radially removed.

FIG. 4B illustrates an example of an electrode pocket formed using the flexible and stretchable pattern of FIG. 4A. FIG. 4B illustrates a shape of a microelectrode pocket structure to measure a physiological signal of a 3D cell 400 by the electrophysiological signal measurement apparatus 10 shown in FIG. 4A. The electrophysiological signal measurement apparatus 10 may ensure flexibility and stretchability using the cantilever structure, to effectively enclose the 3D cell 400 and to accurately measure an electrophysiological signal.

Also, a mesh-shaped microelectrode array based on a serpentine structure may also be applicable to the electrophysiological signal measurement apparatus 10. An electrode array may have a shape of an array of protrusions on which a conductor is formed.

By adjusting geometric parameters such as a thickness and a width of a serpentine structure and a cantilever structure, a size, flexibility and stretchability of the electrophysiological signal measurement apparatus 10 may be adjusted, and a microelectrode pocket suitable for characteristics of cells to be cultured may be formed.

Figure 5:
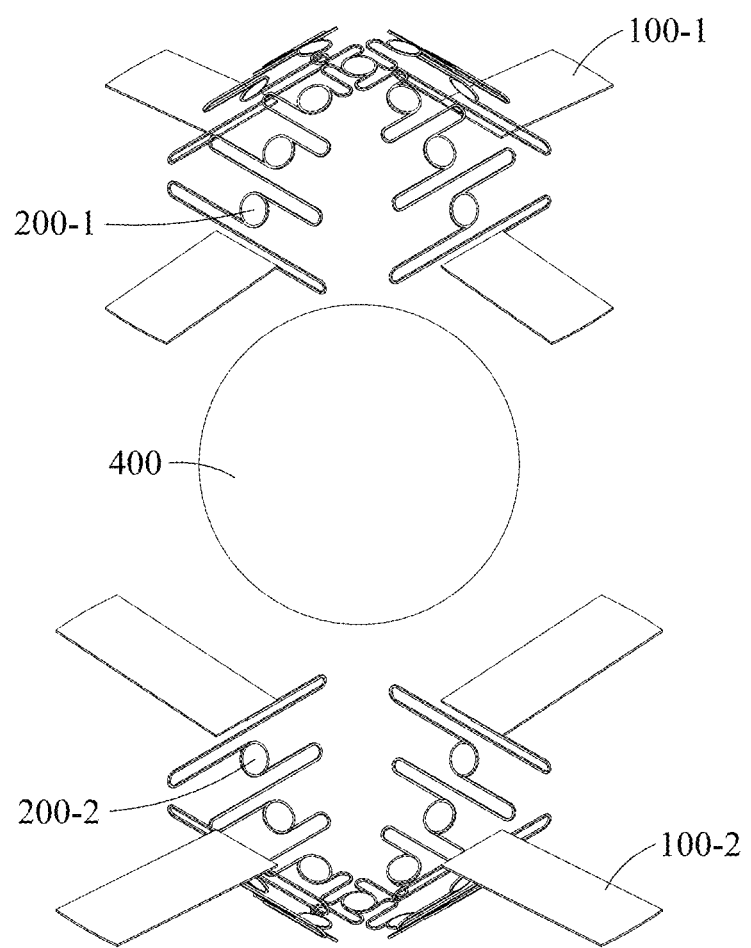
FIG. 5 illustrates an example of an electrophysiological signal measurement apparatus including an electrode pocket structure formed using two flexible substrates.
Figure 6:
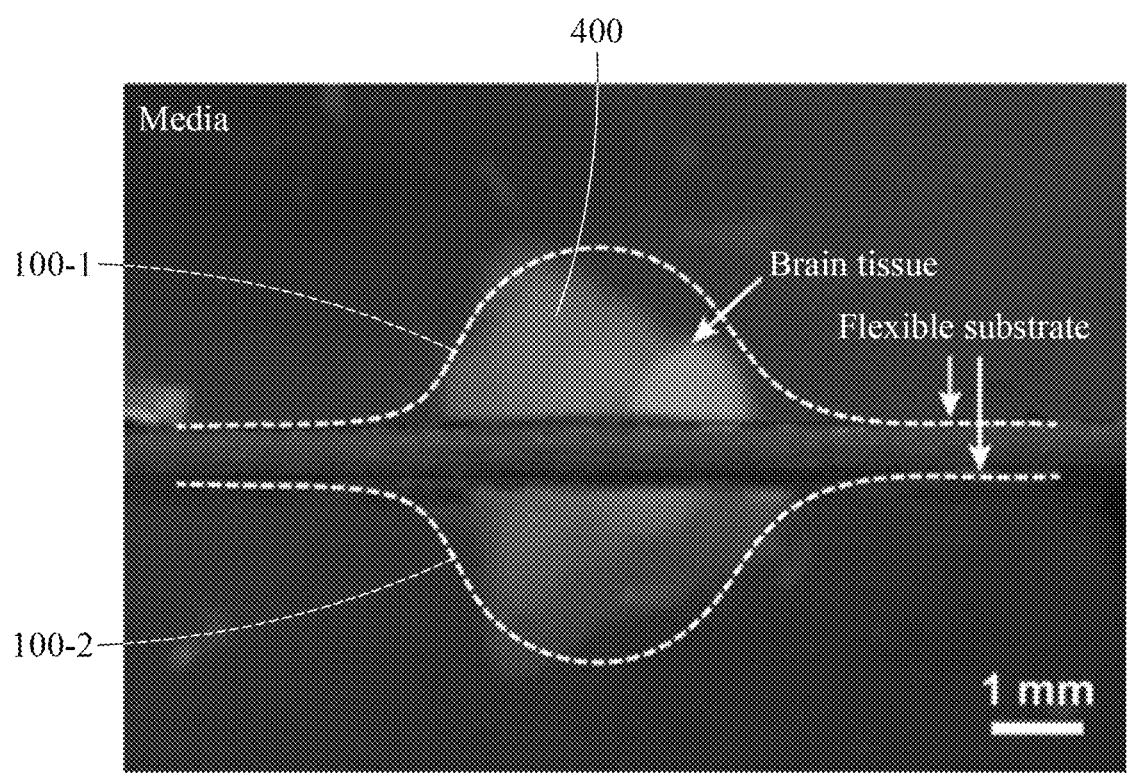
FIG. 6 illustrates an example of an electrophysiological signal measurement apparatus that encloses a brain tissue of a laboratory rat.

FIG. 5 illustrates an example of an electrophysiological signal measurement apparatus including an electrode pocket structure formed using two flexible substrates, and FIG. 6 illustrates an example of an electrophysiological signal measurement apparatus that encloses a brain tissue of a laboratory rat.

Referring to FIGS. 5 and 6, an electrophysiological signal measurement apparatus 10 may include an electrode pocket formed by combining a plurality of flexible substrates, for example, a first flexible substrate 100-1 and a second flexible substrate 100-2.

The electrophysiological signal measurement apparatus 10 may include the first flexible substrate 100-1 and the second flexible substrate 100-2. The first flexible substrate 100-1 may include a plurality of protrusions 200-1, and the second flexible substrate 100-2 may include a plurality of protrusions 200-2. Conductors 300 may be formed on the plurality of protrusions 200-1 and 200-2.

Regions other than the protrusions 200-1 and 200-2 may be partially removed from the first flexible substrate 100-1 and the second flexible substrate 100-2. Materials of the first flexible substrate 100-1 and the second flexible substrate 100-2 may be the same as those described with reference to FIGS. 1A and 1B. Materials of the conductors 300 may also be the same as those described with reference to FIGS. 1A and 1B.

The first flexible substrate 100-1 and the second flexible substrate 100-2 may each have a pattern of a serpentine structure or a cantilever structure, as described above. Also, the first flexible substrate 100-1 and the second flexible substrate 100-2 may have other flexible and/or stretchable patterns such as a mesh-shaped microelectrode array.

The electrode pocket structure formed by combining the first flexible substrate 100-1 and the second flexible substrate 100-2 may allow a close contact with a 3D cell. Since a density of cells is similar to a density of media, a weight of the cell may be extremely light due to a large buoyancy in the media.

A relatively low contact pressure between an electrode and a cell may hinder a signal measurement. According to a related art, a contact pressure may be increased by culturing cells in an electrode. However, since a structure of a 3D cell is damaged in the related art, it is impossible to reuse cells for other purposes after measurement.

An electrode pocket insertable into a 3D cell may be formed by combining the first flexible substrate 100-1 and the second flexible substrate 100-2, and thus the electrophysiological signal measurement apparatus 10 may increase a contact pressure between a cell and an electrode in comparison to a single electrode measurement system.

A flexible substrate to which the electrode pocket structure is applicable may have a serpentine structure, a cantilever structure, or a mesh structure with a serpentine shape. In addition, the electrophysiological signal measurement apparatus 10 may have various shapes of flexible and stretchable microelectrode arrays.

FIG. 6 illustrates a microscope image captured by inserting a 3D cell 400 into the electrode pocket of FIG. 5. For example, the 3D cell 400 may be a brain tissue of a laboratory rat. The brain tissue may be inserted into the electrophysiological signal measurement apparatus 10 in a form of a slice. The electrophysiological signal measurement apparatus 10 may be formed by combining the first flexible substrate 100-1 in an upper portion and the second flexible substrate 100-2 in a lower portion.

Hereinafter, a method of fabricating an electrophysiological signal measurement apparatus will be described with reference to FIGS. 7 and 8.

Figure 7:
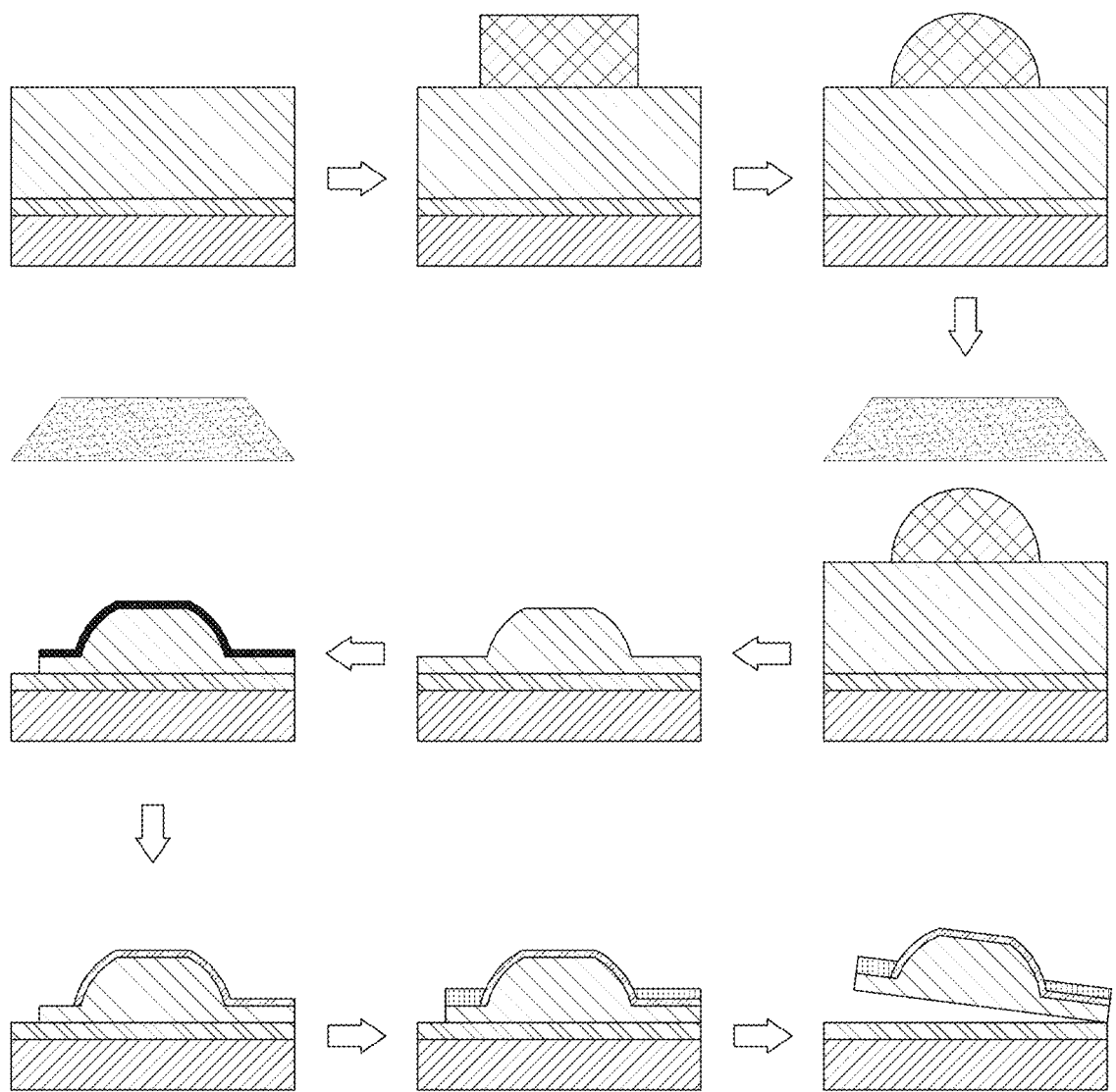
FIG. 7 illustrates a process of fabricating the electrophysiological signal measurement apparatus of FIG. 1A.
Figure 8:
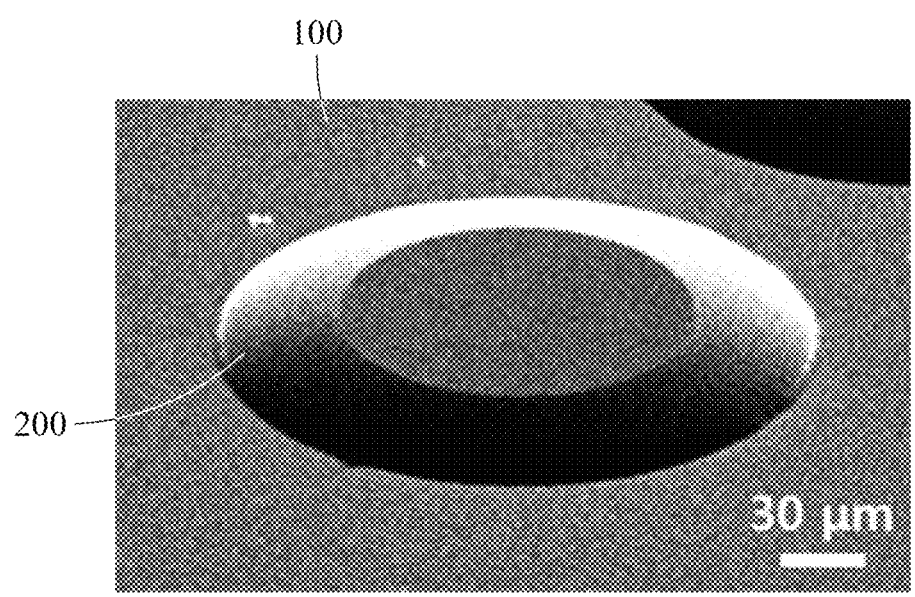
FIG. 8 is a scanning electron microscope image of a protrusion of FIG. 1A.

FIG. 7 illustrates a process of fabricating the electrophysiological signal measurement apparatus 10 of FIG. 1A, and FIG. 8 is a scanning electron microscope image of the protrusion 200 of FIG. 1B.

Referring to FIGS. 7 and 8, the electrophysiological signal measurement apparatus 10 may be fabricated using a MEMS process.

The method of fabricating the electrophysiological signal measurement apparatus 10 may include providing a sacrificial layer 500 under the flexible substrate 100.

The flexible substrate 100 may be formed on the sacrificial layer 500 formed on a silicon substrate 600. For example, the sacrificial layer 500 may be formed with an aluminum layer. Also, metal materials other than aluminum may be appliable to the sacrificial layer 500. An aluminum layer may be deposited by thermal deposition, electron beam deposition, or sputtering.

The method of fabricating the electrophysiological signal measurement apparatus 10 may include forming the flexible substrate 100. The flexible substrate 100 may be formed through spin coating. For example, the flexible substrate 100 may be formed by spin coating a transparent polyimide.

The method of fabricating the electrophysiological signal measurement apparatus 10 may include generating the plurality of protrusions 200 by etching the flexible substrate 100. The forming of the plurality of protrusions 200 may include forming a photoresist layer 700 on the flexible substrate 100.

The photoresist layer 700 may be formed through spin coating, and may be patterned through an exposure process and a development process using a photomask. The exposure process may be performed using ultraviolet light or light with a wavelength less than that of ultraviolet light.

The forming of the plurality of protrusions 200 may include allowing the photoresist layer 700 to overflow by heating (or hard baking) the photoresist layer 700. Through the above overflow process, a slope of the photoresist layer 700 may be allowed to be gentle, and accordingly a photoresist pattern for forming protrusions 200 may be generated.

The allowing of the photoresist layer 700 to overflow may include adjusting the slope of the photoresist layer 700 based on a heating time and a heating temperature.

The photoresist layer 700 with the adjusted slope may function as a mask in a subsequent etching process, to generate the protrusions 200.

The forming of the plurality of protrusions 200 may include generating the plurality of protrusions 200 by etching the flexible substrate 100 based on the overflowing photoresist layer 700. For example, the etching of the flexible substrate 100 may include dry etching. The photoresist layer 700 remaining after the etching may be striped.

A protrusion 200 having a gentle slope and a predetermined height through an etching process may be formed. The height of the protrusion 200 may be adjusted by changing a thickness of the flexible substrate 100, a thickness of the photoresist layer 700, or a period of time for the etching process.

Also, the slope of the protrusion 200 may be adjusted by changing a temperature and time for heating (or hard baking) for an overflow of the coated photoresist layer 700.

The method of fabricating the electrophysiological signal measurement apparatus 10 may include partially removing regions other than the plurality of protrusions 200 from the flexible substrate 100. The regions other than the plurality of protrusions 200 may be partially removed through an etching process.

A metal mask layer 800 may be used to etch the flexible substrate 100. A metal mask may include copper, aluminum, or chromium. The metal mask layer 800 may be formed by thermal deposition, electron beam deposition, or sputtering.

The metal mask layer 800 may be formed on a region that is not removed, not on a region that is to be removed from the flexible substrate 100. The metal mask layer 800 may be etched by wet etching or lift-off, so that a pattern may be formed.

When the metal mask layer 800 is formed, the flexible substrate 100 may be etched. Etching of the flexible substrate 100 may include dry etching. When the flexible substrate 100 is etched, the metal mask layer 800 may be removed. The metal mask layer 800 may be removed through a wet etching process using etchant.

When the metal mask layer 800 is removed, the flexible substrate 100 may include the plurality of protrusions 200, and be in a state in which the regions other than the protrusions 200 are partially removed.

The method of fabricating the electrophysiological signal measurement apparatus 10 may include forming the conductor 300 on the plurality of protrusions 200. When the metal mask layer 800 is removed, the conductor 300 may be formed. The conductor 300 may include Au, Ag, Pt, Ti, Ir, and IrOx. The conductor 300 may be formed by electron beam deposition, thermal deposition, and sputtering.

The conductor 300 may be patterned by wet etching or a lift-off scheme. A protruding microelectrode may be generated by forming the conductor 300 on the plurality of protrusions 200.

An insulating layer 750 may be selectively formed on the conductor 300. The insulating layer 750 may be formed using a photoresist. The photoresist may include, for example, SU-8.

The method of fabricating the electrophysiological signal measurement apparatus 10 may include removing the sacrificial layer 500 after the conductor 300 is formed. For example, the sacrificial layer 500 may be removed by an anodic dissolution scheme. In other words, the sacrificial layer 500 may be selectively removed by applying voltage.

Through a removal of the sacrificial layer 500, the silicon substrate 600 and the flexible substrate 100 may be separated.

FIG. 8 illustrates a scanning electron microscope image of a protruding electrode fabricated by an overflow of a photoresist for 3 hours at 85° C.

Hereinafter, an electrophysiological signal measurement apparatus including a culture well will be described with reference to FIGS. 9 through 11B.

Figure 9:
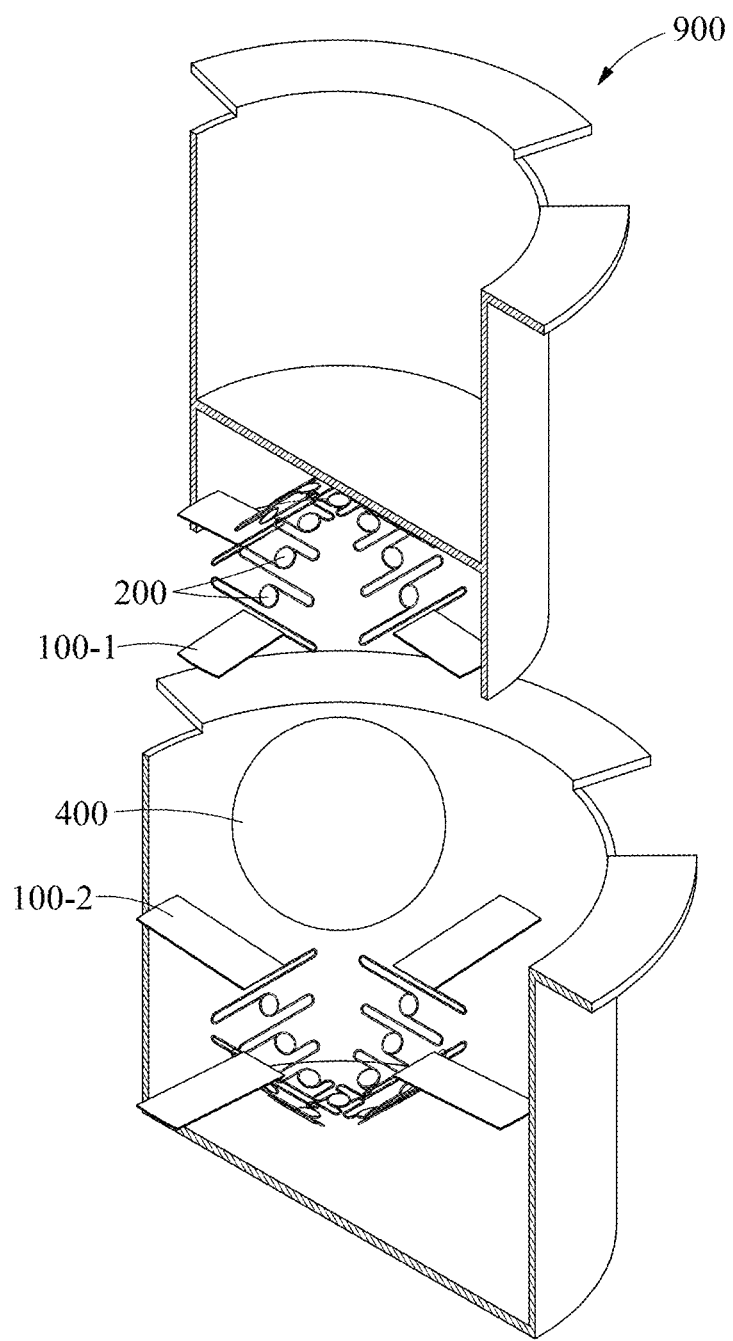
FIG. 9 illustrates an example of an electrophysiological signal measurement apparatus including a transwell.
Figure 10A:
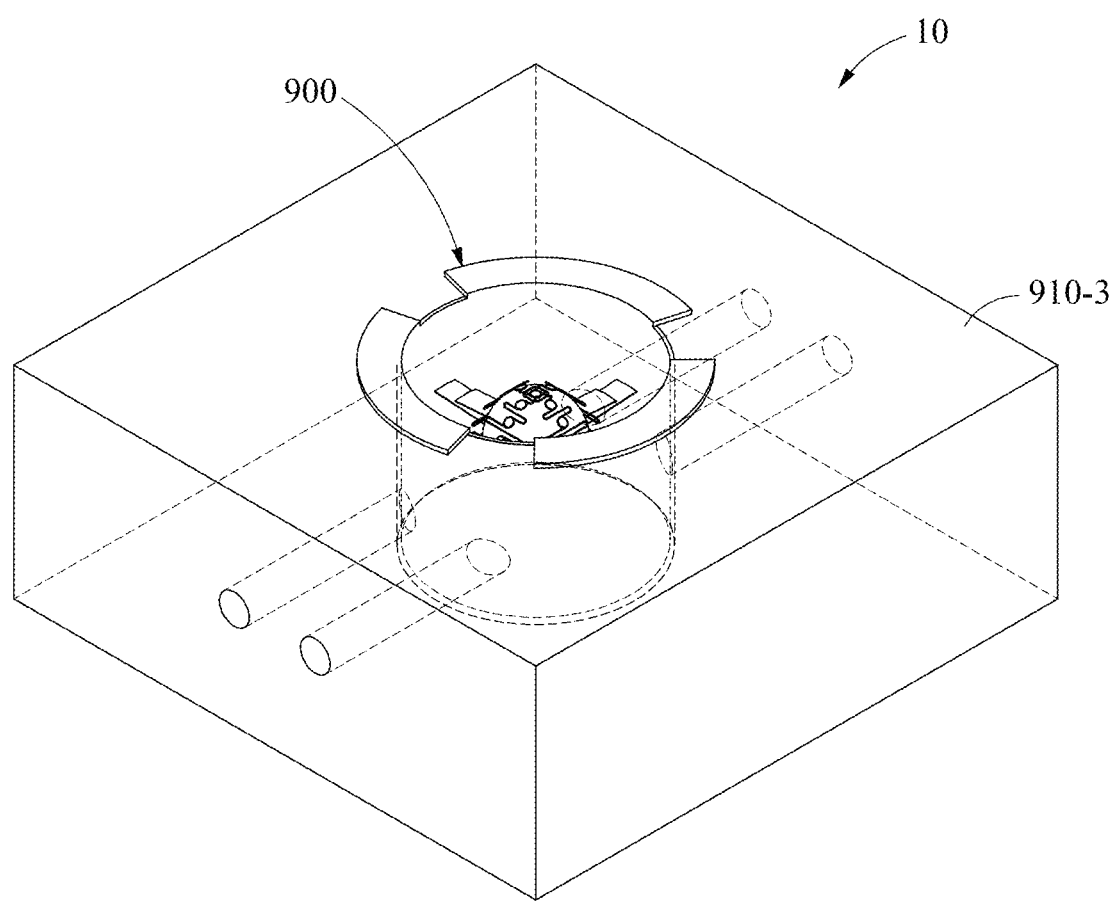
FIG. 10A illustrates an example of an electrophysiological signal measurement apparatus including a culture well.
Figure 10B:
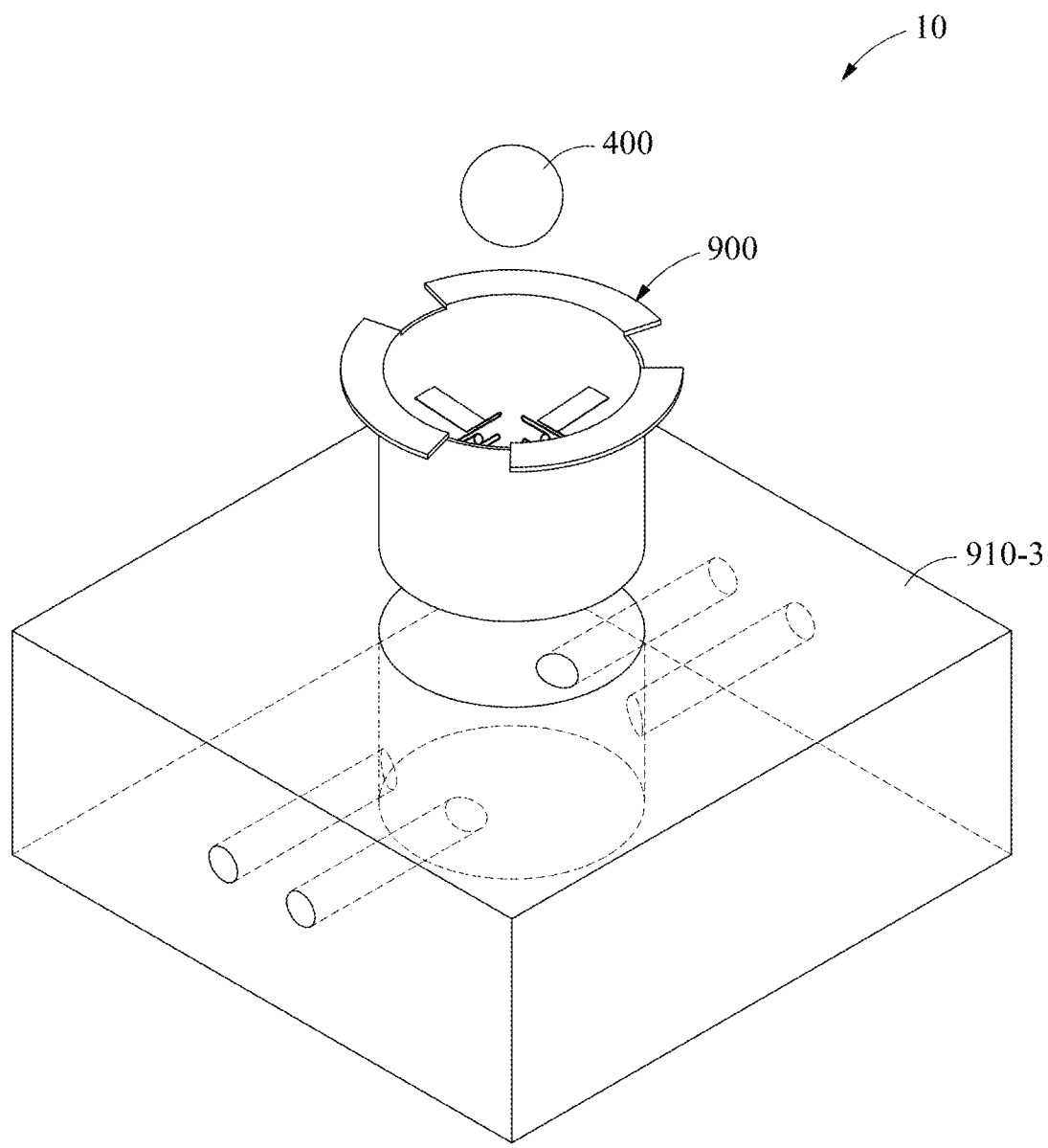
FIG. 10B illustrates a state in which the electrophysiological signal measurement apparatus of FIG. 10A is separated.

FIG. 9 illustrates an example of an electrophysiological signal measurement apparatus including a transwell, FIG. 10A illustrates an example of an electrophysiological signal measurement apparatus including a culture well, and FIG. 10B illustrates a state in which the electrophysiological signal measurement apparatus of FIG. 10A is separated.

Figure 11A:
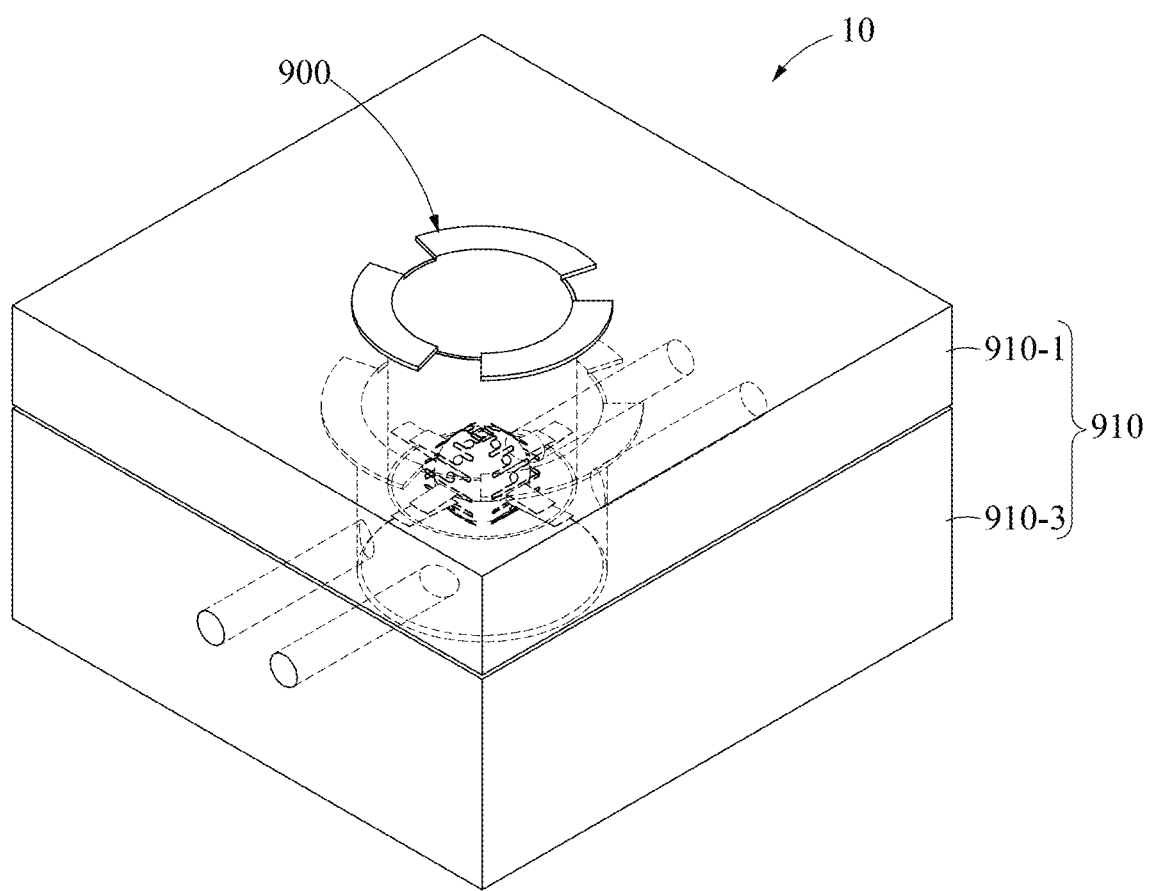
FIG. 11A illustrates an example in which a top plate is coupled to the culture well of FIG. 10A.
Figure 11B:
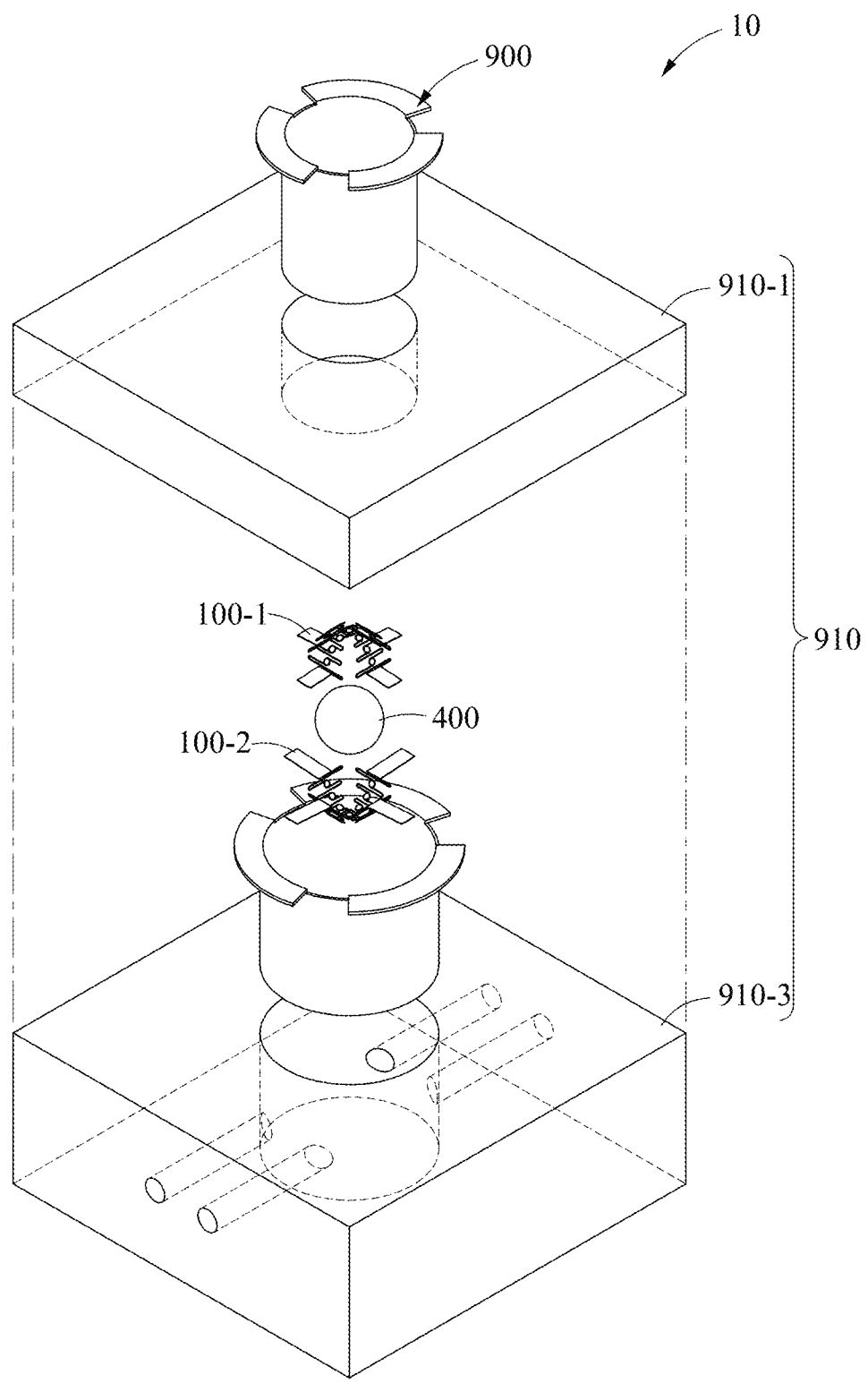
FIG. 11B illustrates a state in which the electrophysiological signal measurement apparatus of FIG. 11A is separated.

FIG. 11A illustrates an example in which an upper plate is coupled to the culture well of FIG. 10A, and FIG. 11B illustrates a state in which the electrophysiological signal measurement apparatus of FIG. 11A is separated.

Referring to FIGS. 9 through 11B, a first flexible substrate 100-1 and a second flexible substrate 100-2 may each include a conductor 300 formed on protrusions 200, and may be coupled to the transwell 900. An electrophysiological signal measurement apparatus 10 may measure an electrophysiological signal of a cell (for example, a 3D cell 400) while culturing the cell using a transwell 900.

The transwell 900 may be coupled to a culture well to culture various cells. The culture well may have various sizes depending on a type of cells and the purpose of culture. For example, the culture well may be 12 wells or 96 wells.

The transwell 900 may include a plastic portion corresponding to a body, and a porous membrane corresponding to a bottom surface. As shown in FIG. 9, the first flexible substrate 100-1 and the second flexible substrate 100-2 may be combined in the body of the transwell 900, and accordingly the 3D cell 400 may be inserted into an electrode pocket formed by combining the first flexible substrate 100-1 and the second flexible substrate 100-2.

An upper plate 910-1 to support the transwell 900 and an upper portion of the transwell 900 may be put as a lid on a lower plate 910-3 coupled to the transwell 900, as shown in FIGS. 10A through 11B, to implement the electrophysiological signal measurement apparatus 10.

The electrophysiological signal measurement apparatus 10 may measure an electrophysiological signal at a desired time through a structure combined with the culture well, and the 3D cell 400 may be transferred to the original culture environment and cultured. As shown in FIGS. 10A through 11B, it is possible to measure an electrophysiological signal by putting a lid corresponding to an upper electrode during culturing of a 3D cell in an electrode pocket formed by coupling the first flexible substrate 100-1 and the second flexible substrate 100-2 in which the conductor 300 is formed on the protrusions 200.

Hereinafter, simulation results of an electrophysiological signal measurement apparatus will be described with reference to FIGS. 12A through 13.

Figure 12A:
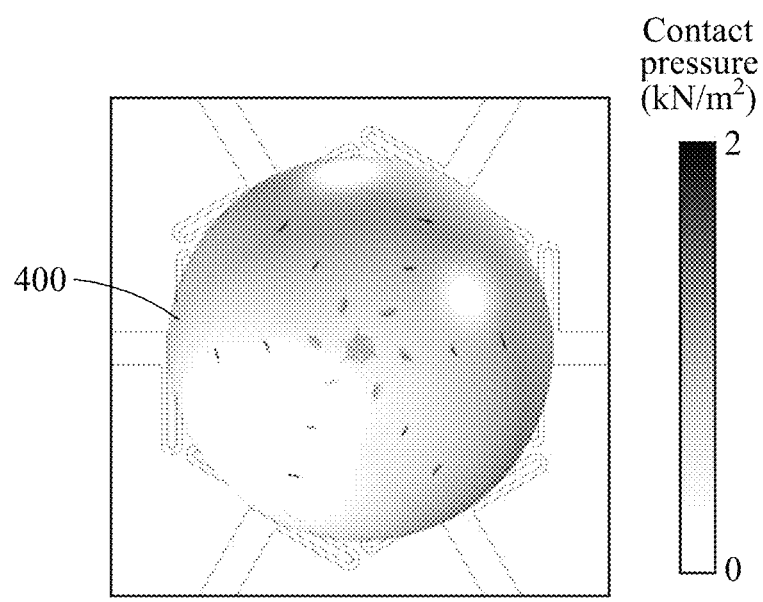
FIG. 12A illustrates a simulation result of a contact pressure with a 3D cell using an electrophysiological signal measurement apparatus without a protrusion.
Figure 12B:
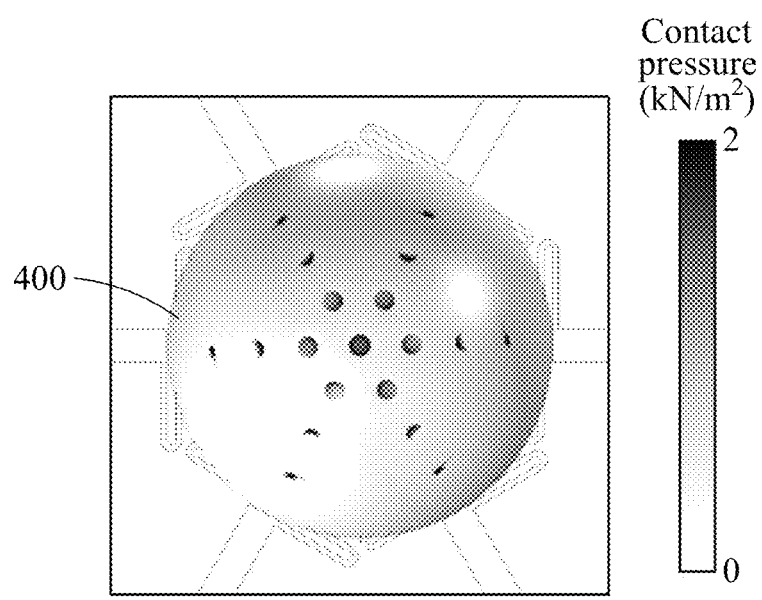
FIG. 12B illustrates a simulation result of a contact pressure with a 3D cell using the apparatus of FIG. 1A.

FIG. 12A illustrates a simulation result of a contact pressure with a 3D cell using an electrophysiological signal measurement apparatus without a protrusion, and FIG. 12B illustrates a simulation result of a contact pressure with a 3D cell using the electrophysiological signal measurement apparatus 10 of FIG. 1A.

Figure 13:
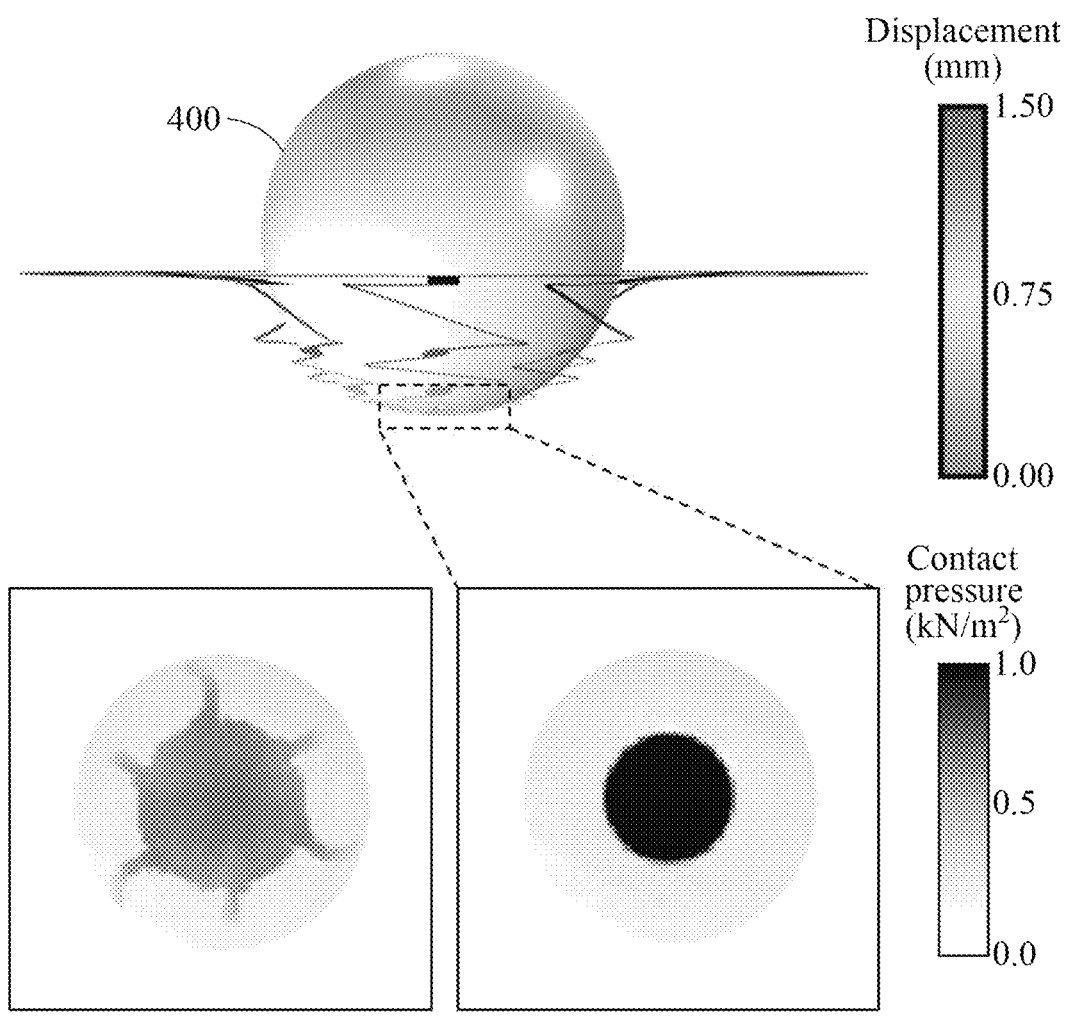
FIG. 13 illustrates simulation results of a displacement and a contact pressure of a conductor when the electrophysiological signal measurement apparatus of FIG. 1A measures an electrophysiological signal of a 3D cell.

FIG. 13 illustrates simulation results of a displacement and a contact pressure of a conductor when the electrophysiological signal measurement apparatus 10 of FIG. 1A measures an electrophysiological signal of a 3D cell.

The electrophysiological signal measurement apparatus 10 may have flexibility and stretchability, and accordingly stably measure an electrophysiological signal by increasing a contact pressure between the 3D cell 400 and the conductor 300 on the protrusions 200. Also, the electrophysiological signal measurement apparatus 10 may minimize a damage to the 3D cell 400 through gentle slopes of the protrusions 200.

As shown in FIGS. 12A and 12B, it may be confirmed that when a protrusion 200 is present, a contact pressure between the electrophysiological signal measurement apparatus 10 and the 3D cell 400 is great in comparison to when a protrusion 200 is absent.

FIG. 13 illustrates simulation results of stretchability (or a displacement) of an electrode when the 3D cell 400 is in the electrophysiological signal measurement apparatus 10 having a flexible and stretchable pattern.

The simulation results of FIG. 13 may be simulation results for an example in which a 3D cell with a dimeter of 3 millimeters (mm) is inserted in an electrode pocket of the electrophysiological signal measurement apparatus 10. In simulations of FIG. 13, results for the second flexible substrate 100-2 are shown.

A lower portion of FIG. 13 illustrates simulation results of contact pressures. In the lower portion of FIG. 13 A, a left image shows a contact pressure in a case in which only a single flexible substrate 100 is applied, and a right image shows a contact pressure in a case in which an electrode pocket structure is formed by combining the first flexible substrate 100-1 and the second flexible substrate 100-2.

The contact pressures for both the cases may be contact pressures at a lowest point of the 3D cell 400.

Figure 14:
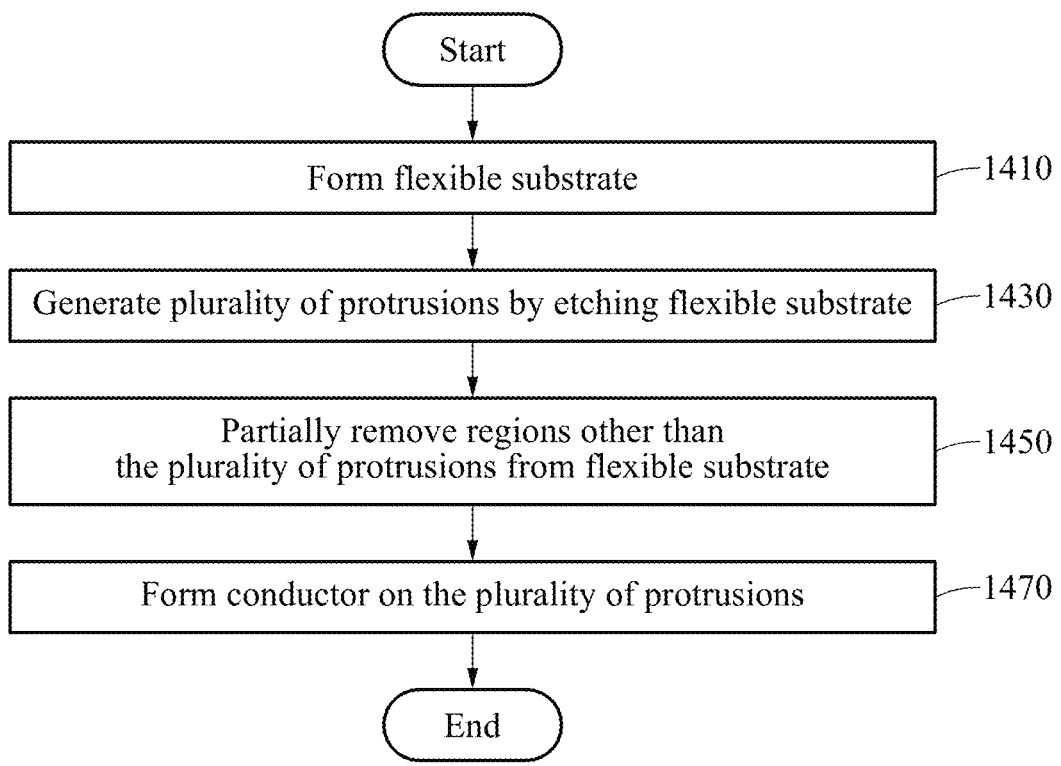
FIG. 14 is a flowchart illustrating a method of fabricating the electrophysiological signal measurement apparatus of FIG. 1A.

FIG. 14 is a flowchart illustrating a method of fabricating the electrophysiological signal measurement apparatus 10 of FIG. 1A.

The method of FIG. 14 may include operation 1410 of forming the flexible substrate 100. The method of FIG. 14 may further include providing a sacrificial layer 500 under the flexible substrate 100.

The method of FIG. 14 may include operation 1430 of generating the plurality of protrusions 200 by etching the flexible substrate 100. Operation 1430 may include forming a photoresist layer 700 on the flexible substrate 100, allowing the photoresist layer 700 to overflow by heating the photoresist layer 700, and generating the plurality of protrusions 200 by etching the flexible substrate 100 based on the overflowing photoresist layer 700.

The allowing of the photoresist layer 700 to overflow may include adjusting a slope of the photoresist layer 700 based on a heating time and a heating temperature.

The method of FIG. 14 may include operation 1450 of partially removing regions other than the plurality of protrusions 200 from the flexible substrate 100.

Operation 1450 may include forming a metal mask layer 800 on the flexible substrate 100 in which the plurality of protrusions 200 are formed, partially etching the regions other than the plurality of protrusions 200 in the flexible substrate 100 based on the metal mask layer 800, and removing the metal mask layer 800.

The method of FIG. 14 may include operation 1470 of forming the conductor 300 on the plurality of protrusions 200. The method of FIG. 14 may further include removing the sacrificial layer 500, after the forming of the conductor 300.

While this disclosure includes specific example embodiments, it will be apparent to one of ordinary skill in the art that various changes in form and details may be made in these example embodiments without departing from the spirit and scope of the claims and their equivalents. The example embodiments described herein are to be considered in a descriptive sense only, and not for purposes of limitation. Descriptions of features or aspects in each example embodiment are to be considered as being applicable to similar features or aspects in other example embodiments. Suitable results may be achieved if the described techniques are performed in a different order, and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. An apparatus for measuring an electrophysiological signal of at least one cell, the apparatus comprising:
   a flexible substrate comprising a plurality of protrusions and a cantilever structure in which the plurality of protrusions are centered; and
   a conductor formed on the plurality of protrusions,
   wherein regions other than the plurality of protrusions are partially removed from the flexible substrate,
   wherein the flexible substrate has a serpentine structure in which the plurality of protrusions are connected to each other via serpentine lines.

2. The apparatus of claim 1, wherein the flexible substrate is formed of a polymer.

3. The apparatus of claim 2, wherein the polymer comprises a polyimide.

4. The apparatus of claim 1, wherein the conductor comprises at least one of gold (Au), silver (Ag), platinum (Pt), titanium (Ti), iridium (Ir), and iridium oxide (IrOx).

5. The apparatus of claim 1, further comprising:
   a cell culture well,
   wherein the flexible substrate is connected to an inner side of the cell culture well.

* * * * *